United States Patent
Wu et al.

(10) Patent No.: US 8,476,311 B2
(45) Date of Patent: Jul. 2, 2013

(54) COMPOSITION FOR TREATING INFLUENZA A ($H_1N_1$) VIRUS AND A PREPARATION METHOD THEREFOR

(75) Inventors: Yang-Chang Wu, Kaohsiung (TW); Fang-Rong Chang, Kaohsiung (TW); Lien-Chai Chiang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 255 days.

(21) Appl. No.: 12/858,595

(22) Filed: Aug. 18, 2010

(65) Prior Publication Data
US 2011/0196029 A1    Aug. 11, 2011

(30) Foreign Application Priority Data
Feb. 11, 2010 (TW) ................................ 99104501 A (51) Int. Cl.
*A01N 43/02* (2006.01)
*A01N 43/16* (2006.01)
*A61K 31/335* (2006.01)
*A61K 31/35* (2006.01)

(52) U.S. Cl.
USPC ............ 514/449; 514/451; 514/453; 514/456

(58) Field of Classification Search
USPC ........................ 514/183, 449, 451, 453, 456
See application file for complete search history.

(56) References Cited

PUBLICATIONS

Abd El-Razek et al., "Sesquiterpene Coumarins from *Ferula foetida*," Journal of the Chinese Chemical Society, 54: 235-238 (2007).
Appendino et al., "Sesquiterpene Coumarin Ethers from Asafetida," Phytochemistry, 35(1): 183-186 (1994).
Yang et al., "Sesquiterpene Coumarins from the Roots of *Ferula sinkiangensis* and *Ferula teterrima*," Chem. Pharm. Bull, 54(11): 1595-1598 (2006).
Zhou et al., "Coumarins and bicoumarin from *Ferula sumbul*: anti-HIV activity and inhibition of cytokine release," Phytochemistry, 53: 689-697 (2000).
Iranshahi et al., "Sesquiterpene coumarins from the fruits of *Ferula badrakema*," Pharmaceutical Biology, 47(4): 344-347 (2009).
Lee et al., "Influenza A (H1N1) Antiviral and Cytotoxic Agents from *Ferula assa-foetida*," J. Nat. Prod., 72: 1568-1572 (2009).

*Primary Examiner* — Yong Chong
(74) *Attorney, Agent, or Firm* — Volpe and Koenig, P.C.

(57) ABSTRACT

New pharmaceutical compositions extracted from *Ferula assa-foetida* are confirmed to effectively treat influenza A ($H_1N_1$) virus. The extraction method of the new pharmaceutical compositions mainly includes steps of (a) extracting *F. assa-foetida* with methanol to obtain a crude extract; (b) fractioning the crude extract with n-hexane-methanol to obtain a methanol extract; (c) fractioning the methanol extract with chloroform-water to obtain a chloroform extract; and (d) chromatographing the chloroform extract to obtain the pharmaceutical compositions, which can be further fractioned and chromatographed to obtain various sesquiterpene coumarins.

8 Claims, 9 Drawing Sheets

COMPOSITION FOR TREATING INFLUENZA A ($H_1N_1$) VIRUS AND A PREPARATION METHOD THEREFOR

FIELD OF THE INVENTION

The present invention relates to a composition for treating influenza A ($H_1N_1$) virus and the preparation method therefor. In particular, it relates to a composition extracted from *Ferula assa-foetida* for treating influenza A ($H_1N_1$) virus and the preparation method therefor.

BACKGROUND OF THE INVENTION

Influenza occurs with seasonal variations and reaches peak prevalence in winter, with many people killed worldwide every year. Until now, only a few organic compounds including amantadine, rimantadine and ribavirin have been used for influenza therapy. However, drug-resistant influenza viruses are generated quickly. The mutation of coat protein genome of influenza viruses severely influenced the antigen expression thereof and new influenza virus mutants are generated. Appearance of Influenza A ($H_1N_1$) virus is one of the examples in recent years.

Influenza A ($H_1N_1$) virus belongs to an influenza virus type A and is grouped as subtype $H_1N_1$ according to haemagglutinin and neuraminidase of the surface antigens. At present, most patients infected with influenza A ($H_1N_1$) virus are dosed with Tamiflu® (oseltamivir), the preferred therapeutic drug. Oseltamivir is a neuraminidase inhibitor, which inhibits the neuraminidase activity of influenza virus types A and B. It prevents the release of new virus particles made from the infected host cells, so that replication and transmission of influenza virus are stopped. At present, Tamiflu-resistant viruses are also appeared. Therefore, preparation of pharmaceutical composition particularly on treating influenza A ($H_1N_1$) virus becomes an important issue.

In addition to the chemical drugs from synthesis, the natural products obtained from medicinal plants also are the opportunity for developing anti-influenza virus drug. According to the anti-virus screen, the extracts of *F. assa-foetida* (Umbelliferae or Apiaceae) showed significant potency against influenza A virus ($H_1N_1$). The roots of this plant originally were an important remedy for "Spanish flu" (type A influenza, $H_1N_1$ subtype) in 1918. However, there is no further researches to explore anti-influenza A virus ($H_1N_1$) activity of the pure compounds from *F. assa-foetida* on within nearly one hundred years.

It is therefore attempted by the applicant to deal with the above situation encountered in the prior art.

SUMMARY OF THE INVENTION

In order to overcome the defect that the commercial drugs cannot efficiently inhibit influenza A ($H_1N_1$) virus, newly extracted sesquiterpene coumarins and diterpenes from *Ferula* sp. are found to efficiently inhibit influenza A ($H_1N_1$) virus activity and show cytotoxicity on human cancer cells. By bioassay-guided fractionation of the methanol extract of *F. assa-foetida*, our finding demonstrates the anti-influenza A virus ($H_1N_1$) activity of this medicinal plants is originated from sesquiterpene coumarins.

A pharmaceutical composition including an effective amount of a sesquiterpene coumarin represented by formula I or II and/or an effective amount of a diterpene represented by formula III is provided in the present invention.

Preferably, the sesquiterpene coumarin and the diterpene are extracted from *Ferula* sp., and the *Ferula* sp. preferably is *Ferula assa-foetida*. The sesquiterpene coumarin represented by formula II inhibits an influenza virus, and the influenza virus includes an influenza A ($H_1N_1$) virus.

Preferably, the pharmaceutical composition of the present invention further can inhibit the growth of a cancer cell line, and the cancer cell line preferably includes a human cancer cell line. Further, the human cancer cell line includes human lung cancer cell line (A549), human breast cancer cell line (MDA-MB-231 and MCF-7), human liver cancer cell line (Hep G2 and Hep 3B) and a human oral cavity cancer cell line (Ca9-22).

A method for preparing a pharmaceutical composition is provided in the present invention. The method includes: (a) extracting a *Ferula* sp. with an methanol to obtain a first extract; (b) partitioning the first extract with an n-hexane-methanol to obtain an methanol extract; (c) partitioning the methanol extract with a chloroform-water to obtain a chloroform extract; and (d) chromatographing the chloroform extract to obtain the pharmaceutical composition.

Preferably, the pharmaceutical composition includes at least a fraction, and the at least a fraction is a sesquiterpene coumarin or a diterpene. The chloroform extract inhibits an activity of an influenza A ($H_1N_1$) virus.

An purpose of the pharmaceutical composition prepared from the aforementioned method is provided in the present invention, and the pharmaceutical composition is performed on inhibiting an activity of an influenza A ($H_1N_1$) virus or a growth of a cancer cell line.

Preferably, the pharmaceutical composition includes 10'R-acetoxy-11'-hydroxyumbelliprenin, 5'-hydroxyumbelliprenin, 10'R-karatavicinol, 8'-acetoxy-5'S-hydroxyumbelliprenin, methyl galbanate, galbanic acid, farnesiferol C, farnesiferol A, conferol, ligupersin A and epi-conferdione when the pharmaceutical composition inhibits the activity of the influenza A ($H_1N_1$) virus, and the pharmaceutical composition includes conferol when the pharmaceutical composition inhibits the growth of the cancer cell line.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

The experimental materials and methods:

I. Experimental Instruments:

Optical rotations were taken on a JASCO-P-1020 polarimeter (cell length 10 mm). UV spectra were measured on a JASCO V-530 UV/vis spectrophotometer. Infrared resonance (IR) spectra were recorded on a Mattson Genesis II FT-IR spectrophotometer. Nuclear magnetic resonance (NMR) spectra were recorded on Varian Gemini-20000 (200 MHz), Varian Unity-plus (400 MHz), and Varian Unity-plus (600 MHz) FT-NMR. NMR spectrometers. Chemical shift ($\delta$) values are in ppm (part per million) with deuterated chloroform (CDCl$_3$) as internal standard, and coupling constants (J) are in Hz. High resolution fast atom bombardment mass spectrum (HRFABMS), high resolution electrospray ionization mass spectrometry (HRESIMS), and electrospray ionization mass spectrometry (ESIMS) measurements respectively were performed on JEOL JMS-700, Bruker APEX II, and Finnigan POLARISQ mass spectrometers. Thin layer chromatography (TLC) was performed on Kieselgel 60 F$_{254}$ (0.20 mm, Merck), and spots were viewed under UV light at 254 nm and 356 nm and/or stained by spraying with 50% H$_2$SO$_4$ and heating on a hot plate. For column chromatography, silica gel (Kieselgel 60, 70-230, and 230-400 mesh, Merck) and Sephadex LH-20 were used. The instrumentation for the reverse phase-medium performance liquid chromatography (RP-MPLC) experiment was composed of a Supelco VersaFlash flash chromatography apparatus and VersaFlash C-18 cartridges (40×150 mm). Further purification of some of compounds obtained was achieved by preparative high performance liquid chromatography (HPLC), using a Shimadzu LC-10ATvp/Shimadzu SCL-10Avp UV-VIS detector and Thermo columns (analytical: 5 μm, 250×4.6 mm; preparative: 8 μm, 250×10 mm; C$_{18}$) were used. For the preparation of Mosher ester derivatives, (S)-(+)- and (R)-(−)-α-methoxy-α-(trifluoromethyl)-phenylacetyl chloride were used as the reagents.

II. Material:

*Ferula assa-foetida* resin (3.23 kg) was purchased from a Chinese herb shop in Taipei, Taiwan.

Figure 1:
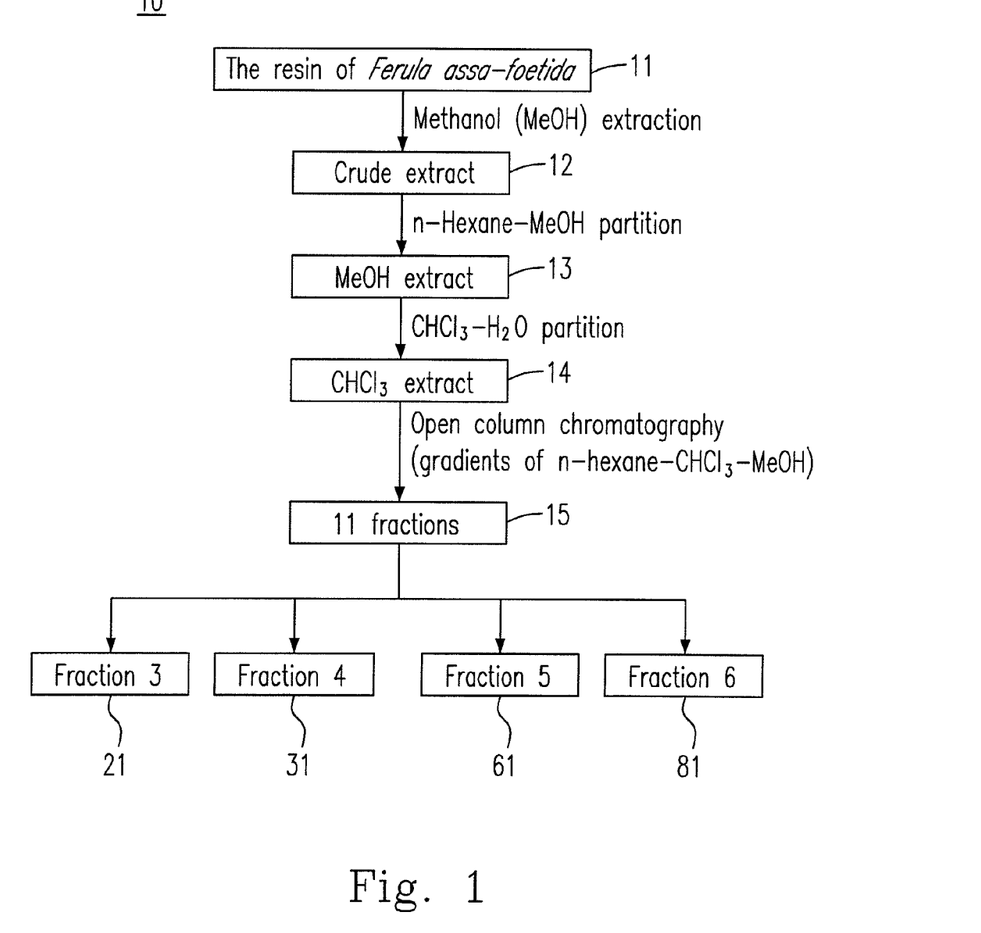
FIG. 1 depicts the flowchart of the fractions extracted from *F. assa-foetida*.

III. Extraction and Isolation:

Please refer to FIG. 1, which depicts the flowchart of the fractions extracted from *F. assa-foetida*. In the method 10, *F. assa-foetida* resin (3.23 kg) was extracted four times with methanol (MeOH, 5 L each) at room temperature (step 11) to obtain a crude extract (313.8 g, step 12). The crude extract was partitioned between n-hexane-methanol (1:1), and then the methanol extract (120.1 g, step 13) was partitioned between chloroform (CHCl$_3$)—H$_2$O (1:1), to obtain a chloroform extract (65.2 g, step 14), which showed significant anti-H$_1$N$_1$ antiviral and cytotoxic activities (referring to the experimental results as follows). Initial fractionation of the chloroform extract (65.2 g) was carried out by open column chromatography on silica gel (230-400 mesh, column: 7×30 cm), using gradients of n-hexane-CHCl$_3$-methanol (100:0:0 to 0:80:20), and gave 11 fractions (step 15). A precipitation was obtained from the first chromatographic step, using n-hexane as the eluent, and was washed with a trace amount of n-hexane to afford oleic acid (2.0 g).

Figure 2:
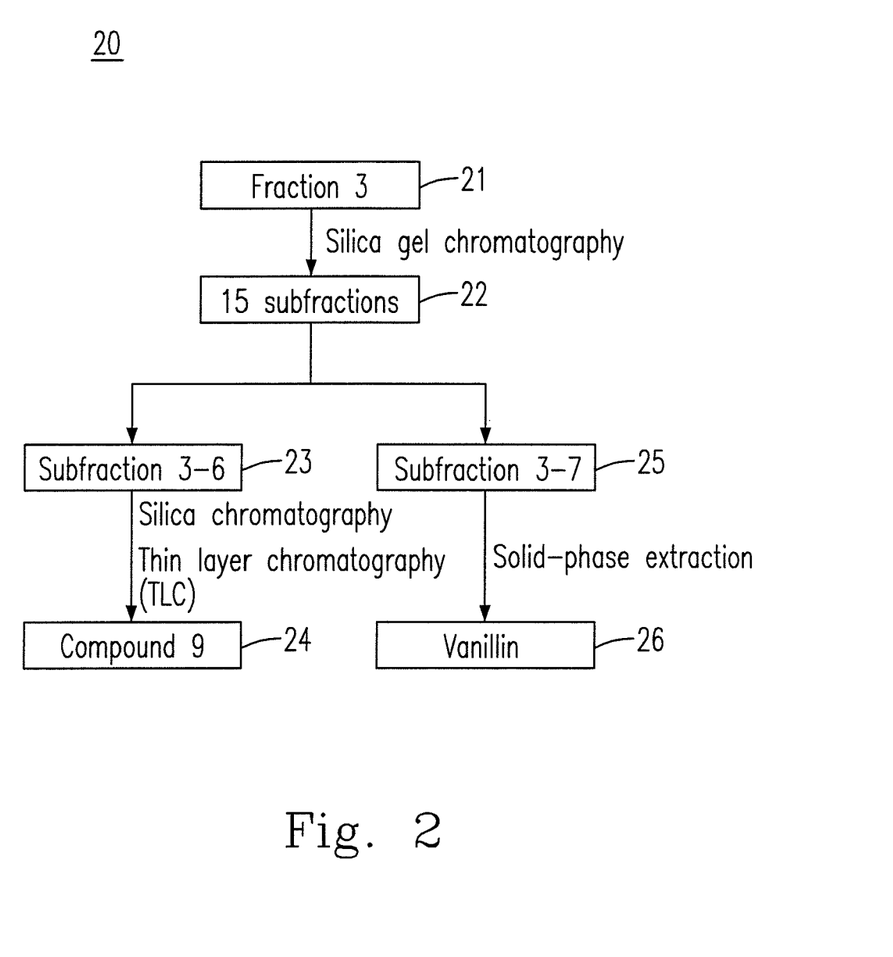
FIG. 2 depicts the further extraction flowchart of Fraction 3 in the present invention.

Please refer to FIG. 2, which depicts the further extraction flowchart of Fraction 3 in the present invention. In the method 20, Fraction 3 (6.66 g, step 21) was fractionated into 15 fractions by silica gel chromatography (70-230 mesh, column: 5×23 cm; CHCl$_3$) (step 22). Subfraction 3-6 (602.06 mg, step 23) was subjected to silica chromatography (70-230 mesh, column: 3×20 cm; n-hexane-ethyl acetate (EtOAc), 1:1) and purified by preparative TLC (CHCl$_3$) to give Compound 9 (1.9 mg, step 24). Subfraction 3-7 (619.90 mg, step 25) was purified by solid-phase extraction (SPE) (DSC-18, 60 mL, 10GMS, No. 52609-U; MeOH—H$_2$O, 80:20) to obtain vanillin (23.5 mg, step 26).

Figure 3:
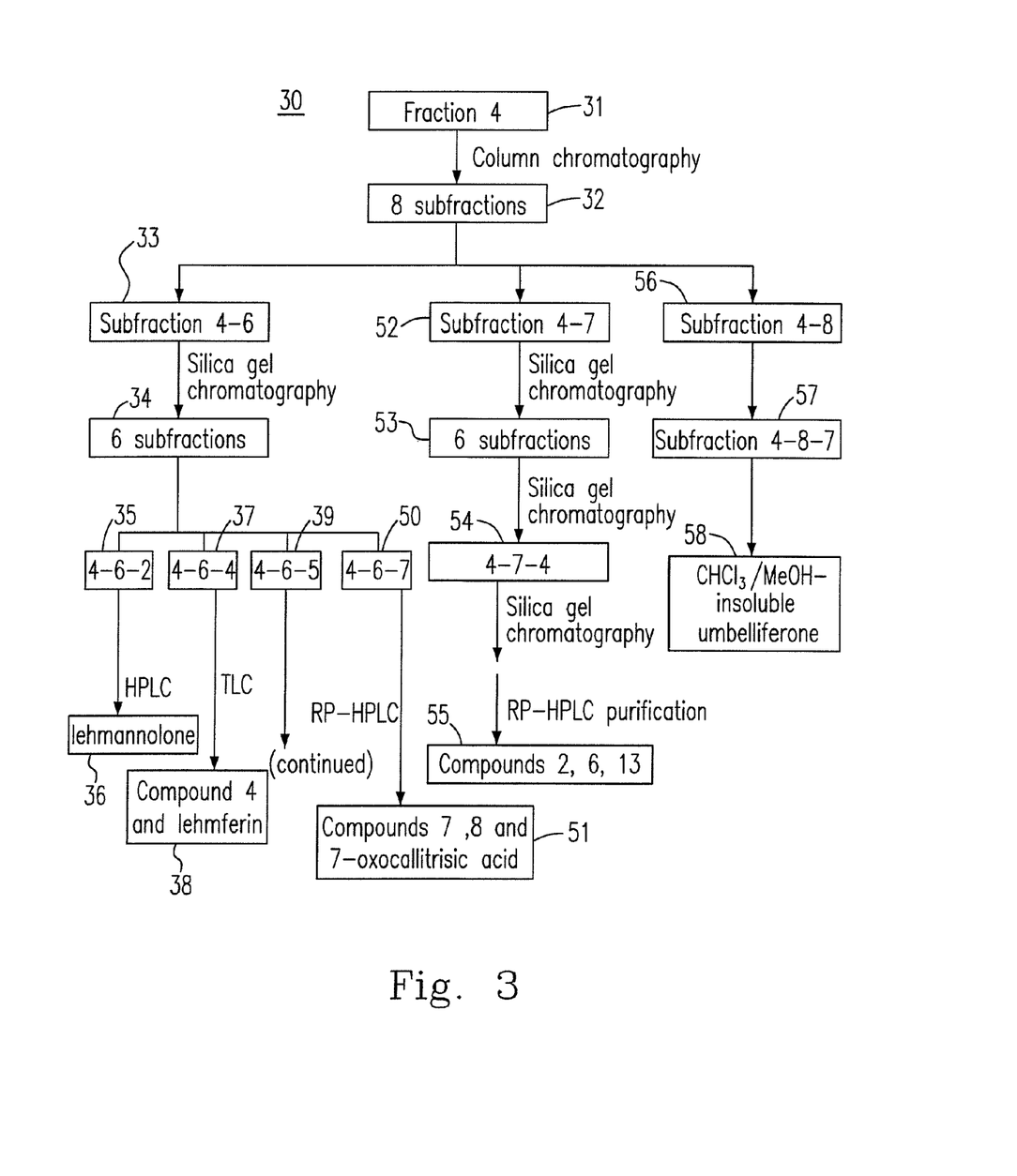
FIG. 3 depicts the further extraction flowchart of Fraction 4 in the present invention.

Please refer to FIG. 3, which depicts the further extraction flowchart of Fraction 4 in the present invention. In the method 30, Fraction 4 (11.78 g, step 31) was separated into 8 subfractions (step 32) by column chromatography on silica gel (70-230 mesh, column: 7×24 cm; n-hexane-EtOAc, 1:1) and crystalline β-sitosterol (0.30 g) was obtained with MeOH. Subfraction 4-6 (step 33) was subjected to silica gel chromatography (70-230 mesh, column: 5×17 cm; CHCl$_3$-MeOH, 60:1) to give 6 subfrations (step 34). Subfraction 4-6-2 (step 35) was purified with HPLC (ODS Thermo®, 10×250 mm; MeOH—H$_2$O, 78:22; flow rate: 3.0 mL/min) to give lehmannolone (1.7 mg, $t_R$=31 min, step 36). Subfraction 4-6-4 (step 37) was purified by preparative TLC (CHCl$_3$) to give Compound 4 (5.7 mg) and lehmferin (2.8 mg, step 38). Subfraction 4-6-5 (400 mg, step 39) was chromatographed on a silica gel column (70-230 mesh, column: 2.5×28 cm), using n-hexane-dichloromethane (CH$_2$Cl$_2$) (2:7) as eluent, and subfraction 4-6-5-1 (253.30 mg, step 40) was purified subsequently with n-hexane-EtOAc (7:2), to obtain 7 subfractions (step 41). Subfractions 4-6-5-1-2 (9.5 mg, step 42), 4-6-5-1-3 (68.7 mg, step 44), and 4-6-5-1-6 (21.9 mg, step 46) were purified by RP-HPLC (flow rate: 3.0 mL/min) to give fetidone B (2.2 mg, MeOH—H$_2$O 70:30, $t_R$=14 min), a farnesiferol B and assafoetidin mixture (16.4 mg, MeOH—H$_2$O 63:37, $t_R$=123 min) (step 43), feselol (3.3 mg, MeOH—H$_2$O 63:37, $t_R$=136 min, step 45), and Compound 1 (2.3 mg, MeOH—H$_2$O 70:30, $t_R$=34 min, step 47), respectively. Subfractions 4-6-5-2 (43.4 mg, step 48) and 4-6-7 (354.7 mg, step 50) were purified by RP-HPLC (MeOH—H$_2$O 76:24; flow rate: 3.0 mL/min) to give (i) Compounds 10 (8.9 mg, $t_R$=38 min) and

11 (6.2 mg, $t_R$=41 min) (step 49), and (ii) Compounds 7 (58.9 mg, $t_R$=27 min), 8 (15.7 mg, $t_R$=31 min) and 7-oxocallitrisic acid (1.5 mg, $t_R$=53 min) (step 51), respectively. Subfraction 4-7 (12.40 g, step 52) was separated by silica gel chromatography (70-230 mesh, column: 5×25 cm; CHCl$_3$-MeOH, 60:1) into 6 subfractions (step 53). Subfraction 4-7-4 (746.80 mg, step 54) was subjected to silica gel chromatography (70-230 mesh, column: 3×20 cm; n-hexane-EtOAc, 5:2) and purified by RP-HPLC (MeOH—H$_2$O, 75:25; flow rate: 3.0 mL/min) to give Compounds 2 (19.7 mg, $t_R$=24 min), 6 (57.0 mg, $t_R$=34 min) and 13 (11.6 mg, $t_R$=12 min) (step 55). The CHCl$_3$/MeOH-insoluble umbelliferone (3.4 mg, step 58) was obtained from subfraction 4-8-7 (58.2 mg, step 57).

Figure 4:
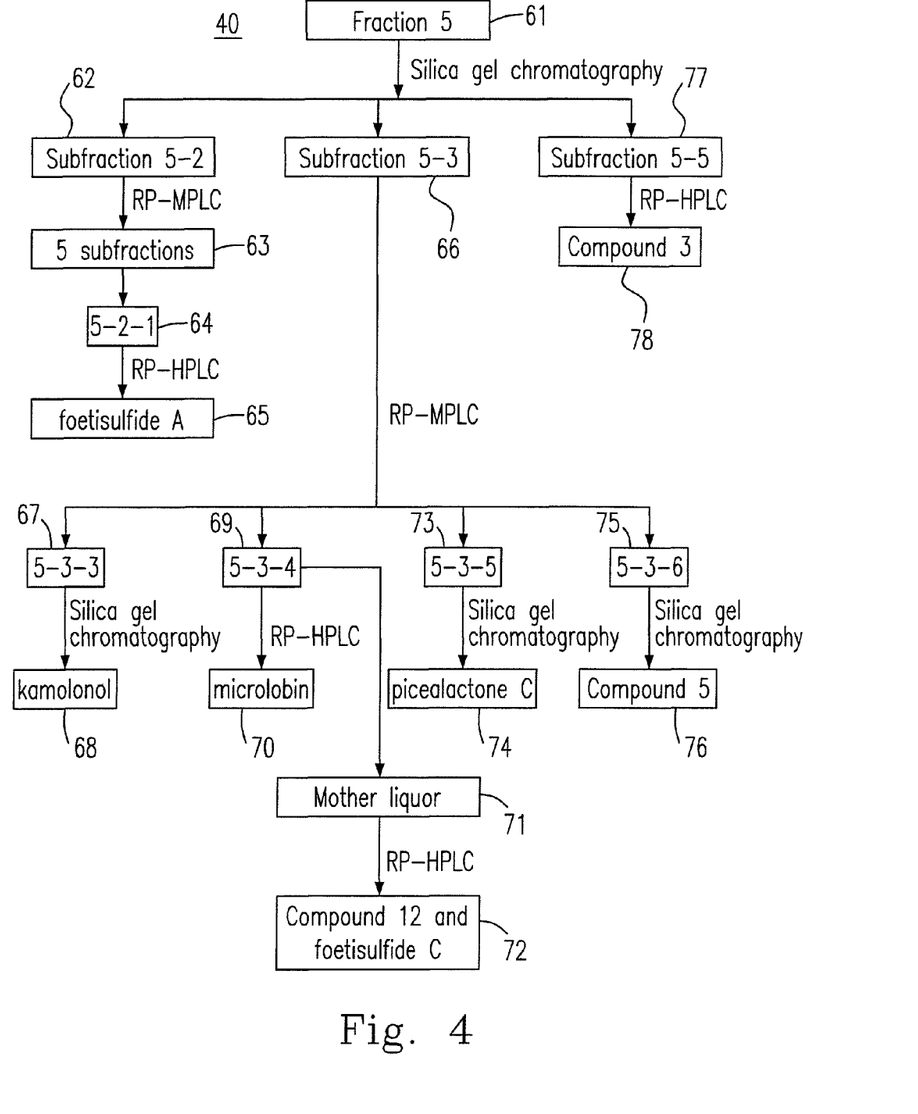
FIG. 4 depicts the further extraction flowchart of Fraction 5 in the present invention.

Please refer to FIG. 4, which depicts the further extraction flowchart of Fraction 5 in the present invention. In the method 40, Fraction 5 (11.77 g, step 61) was chromatographed over silica gel (70-230 mesh, column: 5×30 cm; CHCl$_3$-MeOH, 50:1), with subfraction 5-2 (334.30 mg, step 62) then subjected to RP-MPLC (MeOH—H$_2$O, 65:35), to give 5 subfractions (step 63). Subfraction 5-2-1 (step 64) was purified by RP-HPLC (MeOH—H$_2$O, 61:39; flow rate: 3.0 mL/min) to give foetisulfide A (1.5 mg, $t_R$=43 min, step 65). Subfraction 5-3 (255.2 mg, step 66) was subjected to RP-MPLC (MeOH—H$_2$O, 70:30) and subfraction 5-3-3 (112.3 mg, step 67) was purified by silica gel chromatography (70-230 mesh, column: 2.5×30 cm; CH$_2$Cl$_2$-MeOH, 40:1) to obtain kamolonol (14.3 mg, step 68). Subfraction 5-3-4 (351.4 mg, step 69) was chromatographed by RP-HPLC (MeOH—H$_2$O, 65:35; flow rate: 3.0 mL/min) to give microlobin (30.4 mg, $t_R$=73 min, step 70) and then the mother liquor was purified by RP-HPLC (MeOH—H$_2$O, 53:47; flow rate: 3.0 mL/min) to give Compound 12 (21.3 mg, $t_R$=64 min) and foetisulfide C (3.6 mg, $t_R$=50 min) (step 72). Subfractions 5-3-5 (step 73) and 5-3-6 (step 75) were chromatographed over silica gel (70-230 mesh, column: 1.5×25 cm; CH$_2$Cl$_2$-MeOH, 60:1 and 50:1) to give picealactone C (0.7 mg, step 74) and Compound 5 (241.7 mg, step 76). Subfraction 5-5 (352.3 mg, step 77) was chromatographed by RP-HPLC (MeOH—H$_2$O, 72:28; flow rate: 3.0 mL/min) to give Compound 3 (7.0 mg, $t_R$=16 min, step 78).

Figure 5:
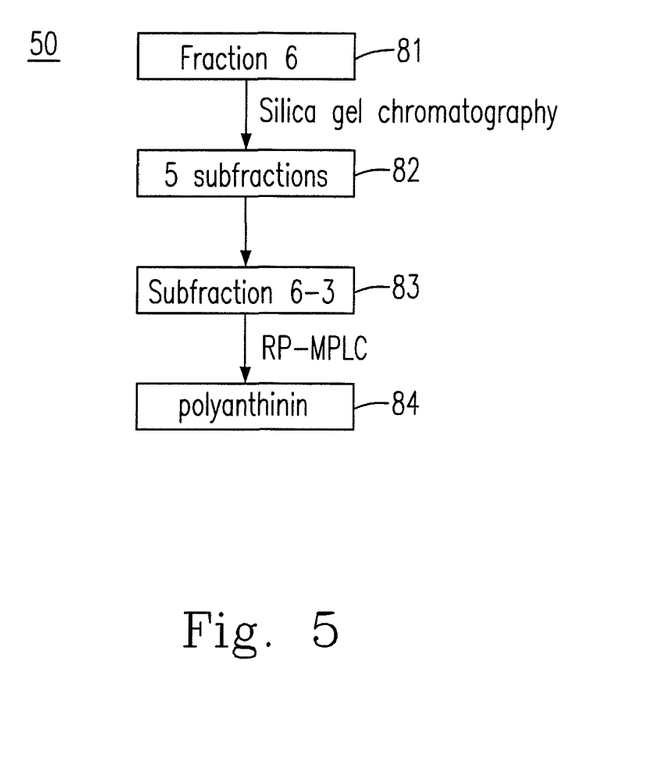
FIG. 5 depicts the further extraction flowchart of Fraction 6 in the present invention.

Please refer to FIG. 5, which depicts the further extraction flowchart of Fraction 6 in the present invention. In the method 50, Fraction 6 (4.33 g, step 81) was chromatographed over silica gel (70-230 mesh, column: 7×35 cm; CH$_2$Cl$_2$-MeOH, 25:1) to give 5 subfractions (step 82). Subfraction 6-3 (step 83) was purified with RP-MPLC (MeOH—H$_2$O, 55:45) to give polyanthinin (23.4 mg, step 84).

The chemical formulas, physical and chemical properties of brand new Compounds 1 (Formula I), 2 (Formula II) and 3 (Formula III) in the present invention are illustrated as follows.

1. Compound 1: 5'-Acetoxy-8'-hydroxyumbelliprenin

Formula I

Physical and chemical properties: yellow oil; $[\alpha]^{25}_D$+8.6 (c 0.12, CHCl$_3$); UV (MeOH) $\lambda_{max}$ (log ε) 211 (4.54), 318 (3.95) nm; IR (neat) $\nu_{max}$ 3440, 1729, 1613, 1555, 1233, 836 cm$^{-1}$; $^1$H and $^{13}$C NMR (CDCl$_3$, 400 MHz), see Table 1; ESIMS m/z 463 [M+Na]$^+$; HRESIMS m/z 463.2099 [M+Na]$^+$ (calcd for C$_{26}$H$_{32}$O$_6$Na, 463.2096).

2. Compound 2: 10'R-Acetoxy-11'-hydroxyumbelliprenin

Formula II

Physical and chemical properties: yellow oil; $[\alpha]^{25}_D$+11.2 (c 0.5, CHCl$_3$); UV (MeOH) $\lambda_{max}$ (log ε) 213 (4.77), 321 (4.39) nm; IR (neat) $\nu_{max}$ 3480, 1731, 1613, 1555, 1234, 836 cm$^{-1}$; $^1$H and $^{13}$C NMR (CDCl$_3$, 400 MHz), see Table 1; ESIMS m/z 465 [M+Na]$^+$; HRFABMS m/z 443.2433 [M+H]$^+$ (calcd for C$_{26}$H$_{34}$O$_6$+H, 443.2434).

3. Compound 3: 15-Hydroxy-6-en-dehydroabietic Acid

Formula III

Physical and chemical properties: yellow oil; $[\alpha]^{25}_D$−14.6 (c 0.16, CHCl$_3$); UV (MeOH) $\lambda$max (log ε) 243 (3.95), 271 (3.74) nm; IR (neat) $\nu_{max}$ 3417, 1696, 1613, 1514 cm$^{-1}$; $^1$H and $^{13}$C NMR (CDCl$_3$, 400 MHz), see Table 2; ESIMS m/z 337 [M+Na]$^+$; HRESIMS m/z 337.1784 [M+Na]$^+$ (calcd for C$_{20}$H$_{26}$O$_3$Na, 337.1780).

IV. Anti-Influenza A Virus (H$_1$N$_1$) Bioassay:

Madin-Darby canine kidney (MDCK) cells (ATCC CCL34) were used as target cells for viral infection in the XTT (tetrazolium hydroxide salt) assay. MDCK cells were grown as adherent cells in MEM medium supplemented with 10% fetal calf serum (FCS), 100 U/mL penicillin G, 100 µg/mL streptomycin, and 0.25 µg/mL amphotericin B. In the antiviral assay, the medium was supplemented with 2% FCS and the above-mentioned antibiotics. Virus titers were determined by the cytopathic effect in MDCK cells and expressed as 50% tissue culture infective dose (TCID$_{50}$) values per mL. All viruses were stored at −70° C. until use. The antiviral activity against influenza A virus (H$_1$N$_1$) was evaluated by the XTT method. MDCK cells, treated by trypsin, were seeded onto 96-well plates with a concentration of 1.0×10$^5$ cells/mL and a volume of 70 µL per well. After incubation at 35° C. with 5% CO$_2$ for 24 hours, 20 µL of test virus solution were added and incubated for another 1 hour. Different concentrations of test substances were then added to culture wells in triplicate. Amantadine was used as a positive control. After incubation at 35° C. with 5% $CO_2$ for 3 days, XTT reagent was added and incubated for 3 hours. The viral inhibition rate (%) was calculated as $[100-(OD_{492}/OD_{690})\times100]$%. The antiviral concentration of 50% inhibition ($IC_{50}$) was defined as the concentration achieving 50% cytoprotection against virus infection.

V. Cytotoxicity Bioassays:

Fractions and isolates were tested against lung (A549), breast (MEA-MB-231 and MCF7), liver (HepG2 and Hep3B), and oral (Ca9-22) human cancer cell lines using an established colorimetric MTT (diphenyltetrazolium bromide) assay protocol. Doxorubicin was used as a positive control. In brief, freshly trypsinized cancer cell suspensions were seeded in 96-well microtiter plates at densities of 5,000-10,000 cells per well with test compounds added from a dimethyl sulfoxide (DMSO) stock solution. After 3 days in culture, the attached cells were incubated with MTT (0.5 mg/mL, 1 hour) and subsequently solubilized in DMSO. The absorbance was measured at 550 nm using an ELISA reader. The $IC_{50}$ is the concentration of agent that reduced cell growth by 50%, under the experimental conditions used.

Experimental Results:

For conveniently illustrating Compounds 1 to 13 extracted in the present invention, the structural formulas (I to XIII) corresponding to Compounds 1 to 13 are listed as follows.

Formula I

Formula II

Formula III

Formula IV

Formula V

Formula VI

Formula VII

Formula VIII

Formula IX

Formula X

Formula XI

Formula XII

Formula XIII

A MeOH extract of the resin of *F. assa-foetida* was partitioned between n-hexane-MeOH (1:1) and then the MeOH layer was partitioned between $CHCl_3$-$H_2O$ (1:1) to obtain a $CHCl_3$ extract, which showed significant anti-$H_1N_1$ activity ($IC_{50}$<3.4 μg/mL) and cytotoxicity for lung, breast and oral human cancer cell lines ($IC_{50}$<20 μg/mL). Initial fractionation of the $CHCl_3$ extract was carried out by open liquid chromatography on silica gel to give 11 fractions. Chromatographic fractionation of these active subfractions provided two new sesquiterpene coumarins (Compounds 1 and 2), a new diterpene (Compound 3), and 27 known compounds.

1. Compound 1 (5'-acetoxy-8'-hydroxyumbelliprenin)

Figure 6:
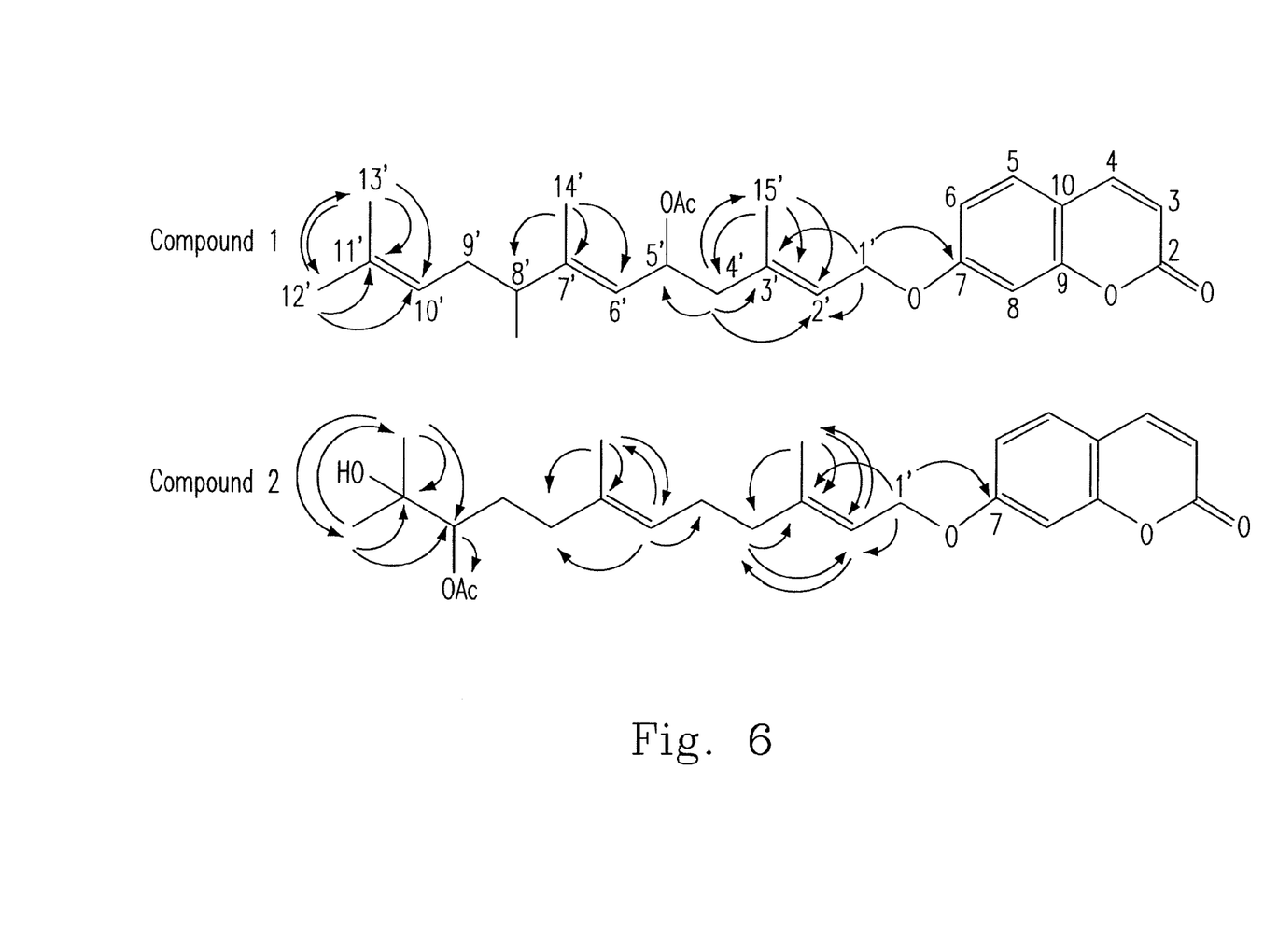
FIG. 6 depicts the HMBC correlations for Compounds 1 and 2.

HRESIMS of Compound 1 exhibited a $[M+Na]^+$ ion at m/z 463.2099 ($C_{26}H_{32}O_6Na$). The IR spectrum showed absorptions for hydroxy (3440 $cm^{-1}$), acetoxy (1729 $cm^{-1}$), and aromatic (1613 and 1555 $cm^{-1}$) functional groups. UV absorptions at 211 and 318 nm also indicated a coumarin nucleus oxygenated at the C-7 position. In the $^{13}C$ NMR spectrum, Compound 1 displayed 26 carbon signals, with nine being typical for an umbelliferone skeleton [(δ 101.5 (C-8), 112.5 (C-10), 113.1 (C-3), 114.2 (C-6), 128.7 (C-5), 143.4 (C-4), 155.8 (C-9), 161.2 (C-2), and 161.9 (C-7)] and the remaining 17 signals ascribable to a sesquiterpene moiety [δ 18.0 (C-13'), 13.1 (C-14'), 17.1 (C-15'), 25.9 (C-12'), 34.2 (C-9'), 44.9 (C-4'), 65.2 (C-1'), 68.9 (C-5'), 75.9 (C-8'), 119.5 (C-10'), 122.1 (C-2'), 123.3 (C-6'), 135.5 (C-11'), 137.6 (C-3'), 141.9 (C-7')] with an acetoxy group (δ 21.2 and 170.3). In the $^1H$ NMR spectrum, signals for two main moieties, a coumarin and a sesquiterpene, were revealed. The coumarin moiety appeared as 5 signals [$δ_H$ 6.24 and 7.63 (each 1H, d, J=9.4 Hz), 7.35 (1H, d, J=8.4 Hz), 6.82 (1H, dd, J=2.4, 8.4 Hz), 6.79 (1H, d, J=2.4 Hz)]. In turn, the sesquiterpene moiety displayed signals for 4 methyls [$δ_H$ 1.62, (3H, brs), 1.71 (3H, brs), 1.72 (3H, brs), 1.81, (3H, s)], 2 methylenes [$δ_H$ 2.23 (2H, m), 2.28 (1H, d, J=6.0 Hz), 2.45 (1H, dd, J=7.6, 13.6 Hz)], an oxygenated methylene [$δ_H$ 4.57 (2H, d, J=6.2 Hz)], 3 olefinic methines [$δ_H$ 5.08 (1H, brt, J=6.4 Hz), 5.41 (1H, d, J=8.8 Hz), 5.50 (1H, brt, J=6.2 Hz)], and 2 oxygenated methines [$δ_H$ 3.99 (1H, brt, J=6.4 Hz), 5.70 (1H, m)]. Compound 1 gave the same molecular formula, $C_{26}H_{32}O_6$, and similar 1D NMR data to Compound 6 (8'-acetoxy-5'-hydroxyumbelliprenin) with the only difference being due to the placement of an acetoxy group and a hydroxy group. The key heteronuclear multiple bond correlation (HMBC) correlations suggested that the acetoxy and hydroxy groups could be positioned at C-5' and C-8', respectively (FIG. 6). The HMBC correlation of an oxygenated methylene $δ_H$ 4.57 (H-1') with a carbon signal at $δ_C$ 161.9 (C-7) indicated that the sesquiterpene unit is attached to C-7 of the coumarin moiety via an ether linkage. The new Compound 1 was therefore assigned as 5'-acetoxy-8'-hydroxyumbelliprenin.

2. Compound 2 (10'R-acetoxy-11'-hydroxyumbelliprenin)

A $[M+H]^+$ ion at m/z 443.2433 ($C_{26}H_{35}O_6$) was present in the HRFABMS of Compound 2. IR spectrum showed absorptions for hydroxy (3480 $cm^{-1}$), acetoxy (1731 $cm^{-1}$), and aromatic (1613 and 1555 $cm^{-1}$) functional groups. UV absorptions at 213 and 321 nm indicated a coumarin nucleus oxygenated at the C-7 position. In the 1D NMR spectrum (Table 1), the signals indicated a carbon skeleton with two main moieties, a coumarin and a sesquiterpene. On the basis of HMBC correlations [$δ_H$ 4.59 (H-1')/$δ_C$ 162.1 (C-7), 118.4 (C-2'), and 142.3 (C-3'); $δ_H$ 4.77 (H-10')/$δ_C$ 171.2 (O $COCH_3$); $δ_H$ 1.17 (H-12')/$δ_C$ 79.5 (C-10'), 72.4 (C-11'), and 26.7 (C-13'); $δ_H$ 1.18 (H-13')/$δ_C$ 79.5 (C-10'), 72.4 (C-11'), and 24.8 (C-12')], the sesquiterpene unit could be attached to C-7 (δ 162.1) of the coumarin moiety via an ether linkage, and the acetoxy and hydroxy groups were positioned at C-10' (δ 79.5) and C-11' (δ 72.4), respectively. Compound 2 was elucidated as 10'-acetoxy-11'-hydroxyumbelliprenin.

Figure 8:
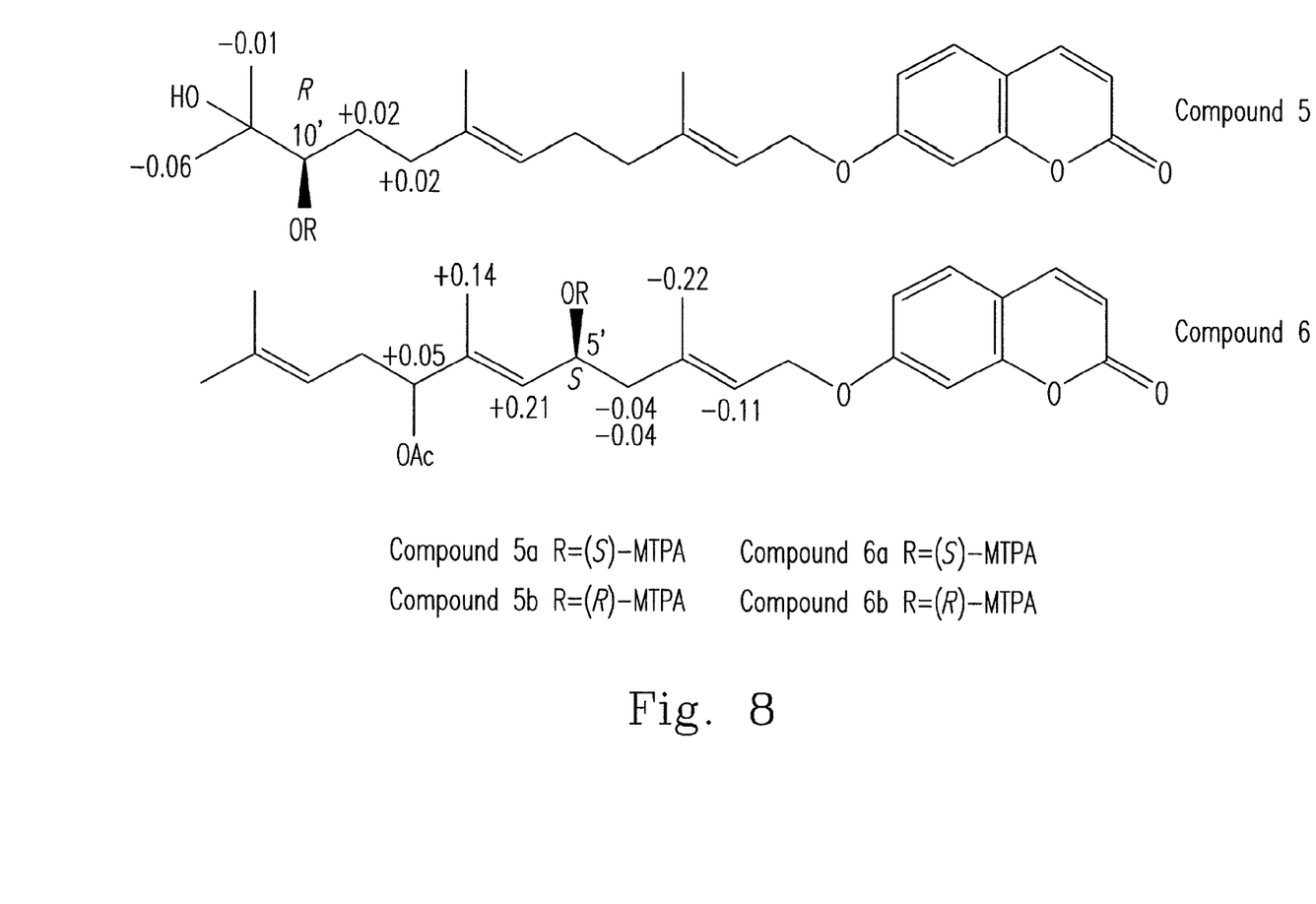
FIG. 8 depicts the $^1$H NMR chemical shift differences [$\Delta\delta = \delta\ H_{(S)-MTPA} - \delta_{(R)-MTPA}$ (ppm)] of the MTPA esters of Compounds 5 and 6.

To determine the only chiral center at C-10', Compounds 2 and 5 (10'-karatavicinol) possess the same biogenetic origin is speculated. Compound 5 was treated separately with (R)- and (S)-α-methoxy-α-(trifluoromethyl)-phenylacetyl chloride [(R)- and (S)-MTPA-Cl] in the presence of $C_5D_5N$, to yield the (S)- and (R)-MTPA esters (FIG. 8), respectively. The MTPA esters were generated successfully at C-10' as elucidated from the $_1H$ NMR spectra (Compound 5a, H-8' δ 2.15, H-9'δ 2.15, H-10' δ 5.49, H-12' δ 1.37, H-13' δ 1.70; Compound 5b, H-8' δ 2.13, H-9' δ 2.13, H-10' δ 5.50, H-12' δ 1.43, H-13' δ 1.71). The differences between the $^1H$ NMR chemical shifts for 5a and 5b (Δ values shown in FIG. 8) led to the assignment of the R-configuration at C-10' of Compound 5. From a comparison of the specific rotation data of Compounds 5 ($[α]^{25}_D$+16.2) and 2 ($[α]^{25}_D$+11.2), the absolute configuration of Compound 2 at C-10' could therefore be assigned with a R configuration. Compound 2 was established as 10'R-acetoxy-11'-hydroxyumbelliprenin.

3. Compound 3 (15-hydroxy-6-en-dehydroabietic Acid)

Figure 7:
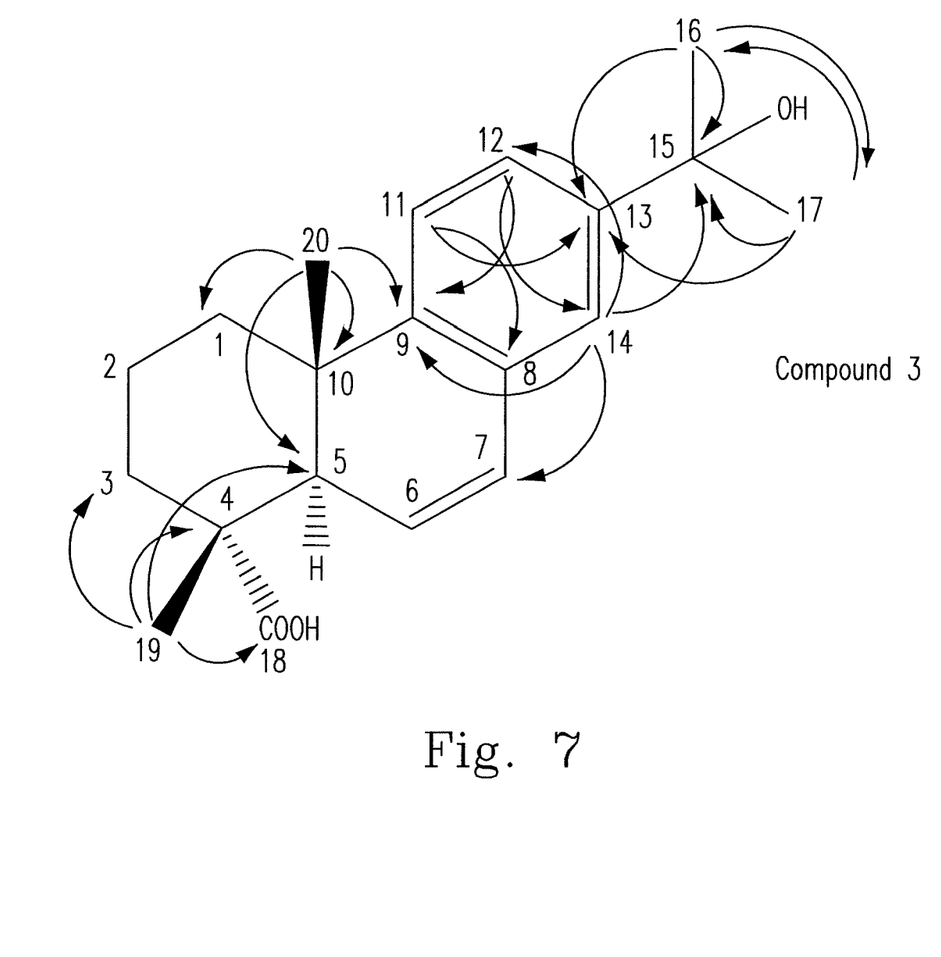
FIG. 7 depicts the HMBC correlations for Compound 3.

Compound 3 gave the molecular formula, $C_{20}H_{26}O_3$, as determined by HRESIMS (m/z 337.1784 $[M+Na]^+$), indicating 8 degrees of unsaturation. Its IR spectrum showed absorptions attributable to hydroxy (3417 $cm^{-1}$), carboxylic acid (1696 $cm^{-1}$), and aromatic ring (1613 and 1514 $cm^{-1}$) functions. Based on its $^{13}C$ NMR and DEPT (distortionless enhancement by polarization transfer data), Compound 3 showed 20 carbon signals, including 4 methyls ($δ_C$ 17.7, 20.7, 31.6, 31.6), 3 methylenes ($δ_C$ 18.3, 35.2, 35.6), 6 methines ($δ_C$ 46.3, 121.6, 122.8, 123.7, 128.3, 130.0), and 7 quaternary ($δ_C$ 37.1, 46.0, 72.4, 132.4, 145.9, 146.6, 183.5) carbons (Table 2). Among the seven quaternary carbons, one was assigned as a carbonyl carbon at δ 183.5. Therefore, the data supported the presence of one carbonyl, 4 olefins, and 3 ring moieties to fulfill the 8 degrees of unsaturation apparently, and Compound 3 was postulated to be an abietane-type diterpene. The HMBC correlations [$δ_H$ 1.57 (H-16)/$δ_C$ 72.4 (C-15), 31.6 (C-17), and 146.6 (C-13); $δ_H$ 1.57 (H-17)/$δ_C$ 72.4 (C-15), 31.6 (C-16), and 146.6 (C-13); $δ_H$ 1.40 (H-19)/$δ_C$ 35.6 (C-3), 46.0 (C-4), 46.3 (C-5), and 183.5 (C-18)] suggested the hydroxy and carboxylic groups to be located at C-15 (δ 72.4) and C-4 (δ 46.0), respectively (FIG. 7). The NOESY (nuclear overhauser effect spectroscopy) correlation between Me-19 and Me-20 as well as the absence of NOESY correlations between H-5/Me-19 and H-5/Me-20 indicated β and α orientations, respectively, for Me-20 and H-5 (trans A/B ring junction). Compound 3 was therefore elucidated as 15-hydroxy-6-en-dehydroabietic acid. This is the first diterpene with an abietane skeleton from the genus *Ferula*.

The absolute configuration of Compound 6 (8'-acetoxy-5'-hydroxyumbelliprenin) at C-5' was still unknown at the time of the present invention. Compound 6 was treated separately with (R)- and (S)-MTPA-Cl in $C_5D_5N$ to yield the (S)- and (R)-MTPA esters (Compounds 6a and 6b, referring to FIG. 8), respectively. The MTPA esters were generated successfully at C-5' as elucidated from the $^1$H NMR spectra (Compound 6a: H-2' δ 5.58, H-4' a δ 2.37, H-4' b δ 2.31, H-5' δ 6.20, H-6' δ 5.70, H-8' δ 5.35, H-14' δ 1.93, H-15' δ 1.72; Compound 6b: H-2' δ 5.69, H-4' a δ 2.41, H-4' b δ 2.35, H-5' δ 6.13, H-6' δ 5.49, H-8' δ 5.30, H-14' δ 1.79, H-15' δ 1.94). The differences between the $^1$H NMR chemical shifts for Compounds 6a and 6b (Δ values shown in FIG. 8) led to the assignment of the S-configuration at C-5', and Compound 6 was determined as 8'-acetoxy-5'S-hydroxyumbelliprenin.

As to other Compounds 4, 7 to 13 extracted from *F. assa-foetida* in the present invention, according to the literatures, they are assigned as 5'-hydroxyumbelliprenin (formula IV, Appendino et al., 1994), methyl galbanate (formula VII, Appendino et al., 1994; Yang et al., 2006), galbanic acid (formula VIII, Yang et al., 2006), farnesiferol C (formula IX, Abd El-Razek et al., 2007; Yang et al., 2006), farnesiferol A (formula X, Abd El-Razek et al., 2007), conferol (formula XI, Zhou et al., 2000), ligupersin A (formula XII, Iranshahi et al., 2009), epi-conferdione (formula XIII, Abd El-Razek et al., 2007).

4. Anti-$H_1N_1$ Virus Activity and Anti-Cancer Activity of Sesquiterpene Coumarin Regarding the in vitro anti-influenza A ($H_1N_1$) virus assay, the test drugs are the pure 7-O-sesquiterpene coumarins, including Compounds 2 and 4 to 13, with amantadine as the positive control. The results are shown in Table 3. In Table 3, most of these compounds exhibited a higher antiviral potency than amantadine, except for Compounds 2, 5 and 12. Because the structures of many these compounds are quite similar, the results in Table 3 are further discussed as follows. For example, Compound 6 (OH-5, OAc-8') has an additional acetoxy group in comparison with Compound 4 (OH-5'), but Compound 6 was much less potent than Compound 4. Compound 2 (OAc-10') has the same skeleton as Compound 5 (OH-10'), and these two compounds showed a similar potency to the positive control, amantadine. Between Compounds 7 ($COOCH_3$-3') and 8 (COOH-3'), Compound 7 showed better potency than Compound 8, and therefore indicated that methyl esterification of C-3' enhanced the activity in the bioassay used. For the bicyclic-sesquiterpene coumarins, Compounds 12 and 13, a C-3'-carbonyl afforded greater potency than a C-3'-OH in this kind of skeleton. Overall, the present invention has determined that sesquiterpene coumarins from *F. assa-foetida* may serve as promising lead compounds for new drug development against influenza A ($H_1N_1$) viral infection. A standardized plant extract of *F. assa-foetida*, may also be worthy of being further investigated as a new phytomedicine.

Furthermore, please refer to Table 4, the compounds in the present invention were screened in a cytotoxicity assay on the cancer cells with doxorubicin as the positive control. Compound 11 exhibited the best potency ($IC_{50}$ 0.51, 2.6, and 3.4 μg/mL) against HepG2, Hep3B, and MCF-7 tested cancer cell lines, respectively. In addition, Compound 11 also showed high potency influenza activity ($IC_{50}$ 0.47±0.05 μg/mL). The remaining compounds were all inactive for all cancer cell lines ($IC_{50}$>4 μg/mL).

Accordingly, the chloroform extract extracted from *F. assa-foetida* and the further extracted and chromatographed compounds in the present invention can effectively inhibits influenza A ($H_1N_1$) virus, and have cytotoxicity on human cancer cell lines.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

TABLE 1

$^1$H and $^{13}$C NMR Data of Compounds 1 and 2 (400 and 100 MHz in $CDCl_3$, δ in ppm, J in Hz).

| | Compound 1 | | Compound 2 | |
|---|---|---|---|---|
| Position | $δ_H$ (J in Hz) | $δ_C$ | $δ_H$ (J in Hz) | $δ_C$ |
| 2 | | 161.2 (s) | | 161.3 (s) |
| 3 | 6.24 (d, 9.4) | 113.1 (d) | 6.23 (d, 9.4) | 112.9 (d) |
| 4 | 7.63 (d, 9.4) | 143.4 (d) | 7.63 (d, 9.4) | 143.5 (d) |
| 5 | 7.35 (d, 8.4) | 128.7 (d) | 7.35 (d, 8.4), | 128.7 (d) |
| 6 | 6.82 (dd, 8.4, 2.4) | 114.2 (d) | 6.82 (dd, 8.4, 2.4) | 113.2 (d) |
| 7 | | 161.9 (s) | | 162.1 (s) |
| 8 | 6.79 (d, 2.4) | 101.5 (d) | 6.79 (d, 2.4) | 101.5 (d) |
| 9 | | 155.8 (s) | | 155.8 (s) |
| 10 | | 112.5 (s) | | 112.4 (s) |
| 1' | 4.57 (d, 6.2) | 65.2 (t) | 4.59 (d, 6.4) | 65.5 (t) |
| 2' | 5.50 (brt, 6.2) | 122.1 (d) | 5.45 (brt, 6.4) | 118.4 (d) |
| 3' | | 137.6 (s) | | 142.2 (s) |
| 4' | 2.45 (brdd, 13.6, 7.6) 2.28 (d, 6.0) | 44.9 (t) | 2.14-2.06 (2H, m) | 39.3 (t) |
| 5' | 5.70 (m) | 68.9 (d) | 2.14-2.06 (2H, m) | 26.1 (t) |
| 6' | 5.41 (d, 8.8) | 123.3 (d) | 5.09 (brt, 6.2) | 124.2 (d) |
| 7' | | 141.9 (s) | | 134.5 (s) |
| 8' | 3.99 (brt, 6.4) | 75.9 (d) | 1.93 (2H, m) | 36.0 (t) |
| 9' | 2.23 (m) | 34.2 (t) | 1.68 (2H, m) | 27.8 (t) |
| 10' | 5.08 (brt, 6.4) | 119.5 (d) | 4.77 (dd, 10.0, 2.8) | 79.5 (d) |
| 11' | | 135.5 (s) | | 72.4 (s) |
| 12' | 1.62 (brs) | 25.9 (q) | 1.17 (brs) | 24.8 (q) |
| 13' | 1.71 (brs) | 18.0 (q) | 1.18 (brs) | 26.7 (q) |
| 14' | 1.72 (brs) | 13.1 (q) | 1.58 (brs) | 16.0 (q) |
| 15' | 1.81 (s) | 17.1 (q) | 1.74 (brs) | 16.7 (q) |
| OAc | 1.99 (s) (C-5') | 21.2 (q) 170.3 (s) | 2.10 (s) (C-10') | 21.1 (q) 171.2 (s) |

TABLE 2

$^1$H and $^{13}$C NMR Data of Compound 3 (400 and 100 MHz in CDCl$_3$, δ in ppm, J in Hz)

| | Compound 3 | |
|---|---|---|
| position | $δ_H$ (J in Hz) | $δ_C$ |
| 1 | 2.21 (brd, 11.2) | 35.2 (t) |
| 2 | 1.81 (m) | 18.3 (t) |
| 3 | 1.81 (m) | 35.6 (t) |
|   | 1.76 (m) |  |
| 4 |  | 46.0 (s) |
| 5 | 2.91 (t, 2.8) | 46.3 (d) |
| 6 | 5.81 (dd, 9.6, 2.7) | 130.0 (d) |
| 7 | 6.55 (dd, 9.6, 2.9) | 128.3 (d) |
| 8 |  | 132.4 (s) |
| 9 |  | 145.9 (s) |
| 10 |  | 37.1 (s) |
| 11 | 7.13 (d, 8.4) | 121.6 (d) |
| 12 | 7.30 (dd, 8.4, 2.0) | 123.7 (d) |
| 13 |  | 146.6 (s) |
| 14 | 7.17 (d, 2.0) | 122.8 (d) |
| 15 |  | 72.4 (s) |
| 16 | 1.57 (brs) | 31.6 (q) |
| 17 | 1.57 (brs) | 31.6 (q) |
| 18 |  | 183.5 (s) |
| 19 | 1.40 (s) | 17.7 (q) |
| 20 | 1.08 (s) | 20.7 (q) |

TABLE 3

| Compound | IC$_{50}$ (μg/ml) | IC$_{90}$ (μg/ml) |
|---|---|---|
| 2 | 0.94 ± 0.07 | 1.98 ± 0.12 |
| 4 | 0.36 ± 0.03 | 0.62 ± 0.08 |
| 5 | 0.99 ± 0.07 | 2.05 ± 0.14 |
| 6 | 0.81 ± 0.06 | 1.56 ± 0.11 |
| 7 | 0.26 ± 0.03 | 0.44 ± 0.05 |
| 8 | 0.45 ± 0.04 | 0.88 ± 0.07 |
| 9 | 0.29 ± 0.02 | 0.50 ± 0.07 |
| 10 | 0.51 ± 0.04 | 0.64 ± 0.07 |
| 11 | 0.47 ± 0.05 | 0.83 ± 0.09 |
| 12 | 0.86 ± 0.08 | 1.75 ± 0.12 |
| 13 | 0.32 ± 0.02 | 0.37 ± 0.03 |
| Amantadine | 0.92 ± 0.04 | 1.73 ± 0.11 |

TABLE 4

Cytotoxicity result of Compounds 2, 5 to 7, 10 to 11, microlobin, polyanthinin, kamolonol, foetisulfide C and vanillin on cancer cell lines

| | IC$_{50}$ (μg/ml)/Cell line | | | | | |
|---|---|---|---|---|---|---|
| Compound | Hep G2 | Hep 3B | MDA-MB-231 | MCF 7 | Ca9-22 | A 549 |
| 2 | >20 | 19.79 | >20 | >20 | >20 | >20 |
| 5 | >20 | >20 | >20 | 14.27 | >20 | 10.97 |
| 6 | 15.59 | 9.82 | >20 | >20 | 14.23 | >20 |
| 7 | 8.42 | 4.33 | >20 | >20 | 19.08 | >20 |
| 10 | 14.89 | 7.66 | 19.00 | 15.57 | 12.07 | 15.79 |
| 11 | 0.51 | 2.63 | >20 | 3.38 | 6.83 | 9.08 |
| Microlobin | >20 | 16.09 | >20 | >20 | >20 | >20 |
| Polyanthinin | 10.42 | 5.90 | 15.68 | 9.94 | 12.66 | 12.28 |
| Kamolonol | >20 | 17.92 | >20 | >20 | >20 | >20 |
| Foetisulfide C | >20 | 19.21 | >20 | >20 | 16.48 | 9.14 |
| Vanillin | >20 | >20 | >20 | 15.69 | >20 | 16.42 |
| Doxorubicin | 0.16 | 0.41 | 0.46 | 0.43 | 0.14 | 0.35 |

What is claimed is:

1. A pharmaceutical composition comprising an effective amount of a sesquiterpene coumarin represented by formula I:

2. The pharmaceutical composition according to claim 1, wherein the sesquiterpene coumarin is extracted from a *Ferula* sp.

3. The pharmaceutical composition according to claim 2, wherein the *Ferula* sp. is a *Ferula assa-foetida*.

4. A pharmaceutical composition comprising an effective amount of a sesquiterpene coumarin represented by formula II:

5. The pharmaceutical composition according to claim 4, wherein the sesquiterpene coumarin is extracted from a *Ferula* sp.

6. The pharmaceutical composition according to claim 5, wherein the *Ferula* sp. is a *Ferula assa-foetida*.

7. The pharmaceutical composition according to claim 4, wherein the sesquiterpene coumarin inhibits an influenza virus.

8. The pharmaceutical composition according to claim 7, wherein the influenza virus is an influenza A ($H_1N_1$) virus.

* * * * *